(12) United States Patent
Kim

(10) Patent No.: US 11,933,779 B2
(45) Date of Patent: Mar. 19, 2024

(54) BODY FLUID TESTING DEVICE HAVING IMPROVED ILLUMINATION

(71) Applicant: INTIN CO., LTD, Daegu (KR)

(72) Inventor: Ji Hoon Kim, Daegu (KR)

(73) Assignee: INTIN CO., LTD, Daegu (KR)

( * ) Notice: Subject to any disclaimer, the term of this patent is extended or adjusted under 35 U.S.C. 154(b) by 1095 days.

(21) Appl. No.: 16/462,537

(22) PCT Filed: Nov. 21, 2017

(86) PCT No.: PCT/KR2017/013221
§ 371 (c)(1),
(2) Date: May 21, 2019

(87) PCT Pub. No.: WO2018/097565
PCT Pub. Date: May 31, 2018

(65) Prior Publication Data
US 2019/0277830 A1  Sep. 12, 2019

(30) Foreign Application Priority Data

Nov. 22, 2016  (KR) .................. 10-2016-0155780

(51) Int. Cl.
*G01N 33/487* (2006.01)
*A61B 5/00* (2006.01)
(Continued)

(52) U.S. Cl.
CPC ......... *G01N 33/48792* (2013.01); *A61B 5/00* (2013.01); *A61B 5/0077* (2013.01);
(Continued)

(58) Field of Classification Search
CPC .......... G01N 33/48792; G01N 27/327; G01N 33/4875; G01N 27/3273; A61B 5/00;
(Continued)

(56) References Cited

U.S. PATENT DOCUMENTS 10,606,053 B2 *   3/2020   Kim ..................... G01N 21/255
2006/0189895 A1 *   8/2006   Neel ................ A61B 5/150358
600/583

(Continued)

FOREIGN PATENT DOCUMENTS

KR   20-2000-0015504 U    8/2000
KR   10-2012-0140328 A    12/2012
(Continued)

OTHER PUBLICATIONS

International Search Report for PCT/KR2017/013221 dated Mar. 19, 2018 from Korean Intellectual Property Office.

*Primary Examiner* — Yi-Shan Yang
*Assistant Examiner* — Kyle W. Kretzer
(74) *Attorney, Agent, or Firm* — Revolution IP, PLLC (57) ABSTRACT

A body fluid testing device having an improved illumination, includes: a test unit including: a sample part having a sheet portion, with body fluid of a user applied onto a first surface thereof; an illumination part having a light source for providing light to the sample part; a battery for supplying power to the illumination part; and a casing receiving a lens group for magnifying the body fluid applied onto the sheet portion; and a user terminal configured such that a camera takes an image of the sample part magnified by the lens group, prior to analyzing the image by the user terminal.

5 Claims, 10 Drawing Sheets

(51) Int. Cl.
*A61B 10/00* (2006.01)
*G01N 27/327* (2006.01)

(52) U.S. Cl.
CPC ........... *A61B 10/00* (2013.01); *G01N 27/327* (2013.01); *A61B 10/0045* (2013.01); *G01N 33/4875* (2013.01)

(58) Field of Classification Search
CPC ... A61B 5/0077; A61B 10/00; A61B 10/0045; A61B 10/0051; A61B 10/0012; A61B 2010/0025; A61B 2010/008; A61B 2560/0204; A61B 2560/0209
See application file for complete search history.

(56) References Cited

U.S. PATENT DOCUMENTS

| | | | | |
|---|---|---|---|---|
| 2015/0177256 | A1* | 6/2015 | Elder | H04N 23/56 |
| | | | | 348/158 |
| 2015/0268186 | A1* | 9/2015 | Pagels | G01N 33/48792 |
| | | | | 205/792 |
| 2016/0231310 | A1* | 8/2016 | Ayyub | G01N 33/4925 |
| 2017/0119357 | A1* | 5/2017 | Hung | A61B 90/57 |
| 2018/0372714 | A1* | 12/2018 | Chen | H04M 1/21 |
| 2019/0192122 | A1* | 6/2019 | Bodo | A61B 10/0012 |

FOREIGN PATENT DOCUMENTS

| | | | |
|---|---|---|---|
| KR | 10-2013-0130443 A | 12/2013 | |
| KR | 101533343 B1 * | 11/2014 | ........... G01N 33/487 |
| KR | 10-1533343 B1 | 7/2015 | |
| KR | 10-2016-0057481 A | 5/2016 | |

* cited by examiner

BODY FLUID TESTING DEVICE HAVING IMPROVED ILLUMINATION

TECHNICAL FIELD

The present invention relates generally to a body fluid testing device having an improved illumination and, more particularly, to a body fluid testing device having an improved illumination, in which by providing an illumination so as for a test to be conducted at any time regardless of the environment, it is possible to obtain a clear image of body fluid, and to allow the test to be conducted accurately.

BACKGROUND ART

Generally, people should visit a specialized medical institution to check their health state and body state. However, in order to receive diagnosis, people need to set aside time for visiting a specialized medical institution during busy work time, and go through complicated formalities and procedures. Particularly, even though most of these formalities are carried out, it is necessary to wait for a long time to receive the examination, while the actual examination and checkup are performed in a very short time. In other words, it takes a great deal of time and money to receive the examination and checkup, and many inconveniences follow. Thus, most people ignore endurable discomfort, and visit specialized medical institutions only when having unendurable pain or discomfort.

In order to solve the inconvenience, techniques have been developed wherein various types of advanced equipment are used to frequently check one's body state and the result is transmitted to a specialized medical institution via a network. However, techniques that are commercialized and are actually used in practice are extremely rare.

Preferably, the use of a simple tester, which has been used for a long time, continues and is increasingly used by the younger generation due to ease of use, low time and cost, and fast results.

Such a tester detects hormones contained in secretions, or identifies changes in the state of the secretions by using secretions from a human body, e.g., saliva, urine, sweat, etc. The tester utilizes the fact that the body undergoes a change in the state of the component contained in the saliva when a certain condition, for example, a specific disease, an infection, an abnormality of the body such as an ovulatory period, or a specific event occurs. As a commonly used testing means, testers for pregnancy testing, diabetes diagnosis, and blood sugar checking are widely used in various forms. In particular, testers are often used by users because they are relatively accurate, easy to use, and affordable at times when the user wants to use it.

Recently, due to increase in the age at marriage, increase in the stress from social life, lack of exercise, etc., the number of couples who are infertile and have difficulty in becoming pregnant has increased, and thus the use of pregnancy tester has greatly increased. However, the conventional pregnancy tester determines only pregnancy or not and is not helpful for the user who is infertile and has difficulty in becoming pregnant. In other words, the conventional pregnancy tester determines only pregnancy or not, so important matters such as the woman's pregnancy probability, arrival of ovulation period, and the man's fertilization ability cannot be identified through the tester but can only identified only by a medical institution's consultation.

DISCLOSURE

Technical Problem

Accordingly, an object of the present invention is intended to propose a body fluid testing device having an improved illumination, in which a user is able to quickly conduct self-testing and to identify the analysis result any time and any place by using body fluid of the user and connecting the device to a user terminal.

Further, another object of the present invention is intended to propose a body fluid testing device having an improved illumination, in which both women and men can use the device for different test purposes, whereby a woman may identify the period of high pregnancy probability by checking her ovulation period and a man may identify his sperm viability, thereby increasing pregnancy probability.

Further, a further object of the present invention is intended to propose a body fluid testing device having an improved illumination, in which by providing an illumination so as for a test to be conducted at any time regardless of the environment, it is possible to obtain a clear image of body fluid, and to allow the test to be conducted accurately.

Technical Solution

In order to accomplish the above object, according to the present invention, there is provided a body fluid testing device having an improved illumination, the testing device including: a test unit including: a sample part having a sheet portion, with body fluid of a user applied onto a first surface thereof; an illumination part having a light source for providing light to the sample part; a battery for supplying power to the illumination part; and a casing receiving a lens group for magnifying the body fluid applied onto the sheet portion; and a user terminal configured such that a camera takes an image of the sample part magnified by the lens group, prior to analyzing the image by the user terminal.

The testing device may further include a coupling means detachably coupled to the test unit, wherein the test unit is detachably coupled to the user terminal by the coupling means, and the coupling means has a mounting portion which the test unit is mounted to and is provided with a clip hole at a position between the lens group of the test unit and the camera, the coupling means being formed in a shape of a clip.

One of the test unit and the coupling means may be provided with a magnet at a mutual contact portion, and a remaining one of the test unit and the coupling means may be provided with a magnet or an iron piece.

The testing device may further include a reflector provided in the casing for scattering light from the light source.

The illumination part may include an insertion module into which a longitudinal end of the sample part is inserted.

The illumination part may include a circuit board with a circuit for electrically connecting the insertion module, the battery, and the light source together.

The circuit may electrically connect the light source and the battery together when the sample part is inserted into the insertion module.

The sample part may be configured such that the longitudinal end thereof to be inserted into the insertion module is provided with a conductive pattern for completing the circuit for connection of the light source and the battery by being electrically connected to an electrical terminal provided on the insertion module.

Advantageous Effects

The body fluid testing device having an improved illumination according to the present invention is advantageous in that a user is able to quickly conduct self-testing and to identify the analysis result any time and any place by using body fluid of the user and connecting the device to a user terminal.

The body fluid testing device having an improved illumination according to the present invention is further advantageous in that both women and men can use the device for different test purposes, whereby a woman may identify the period of high pregnancy probability by checking her ovulation period and a man may identify his sperm viability, thereby increasing pregnancy probability.

The body fluid testing device having an improved illumination according to the present invention is further advantageous in that by providing an illumination so as for a test to be conducted at any time regardless of the environment, it is possible to obtain a clear image of body fluid, and to allow the test to be conducted accurately.

BEST MODE

Hereinafter, exemplary embodiments of the present invention will be described with reference to the accompanying drawings. In the following description, the same elements will be designated by the same reference numerals although they are shown in different drawings. Further, in the following description of the present invention, a detailed description of known functions and configurations incorporated herein will be omitted when it may make the subject matter of the present invention rather unclear. In the drawing, certain features presented in the drawings are expanded, reduced, or simplified for easy explanation, and the drawings and the constituent elements may not be appropriately illustrated. However, those of ordinary skill in the art could easily understand such detailed matters.

Figure 1:
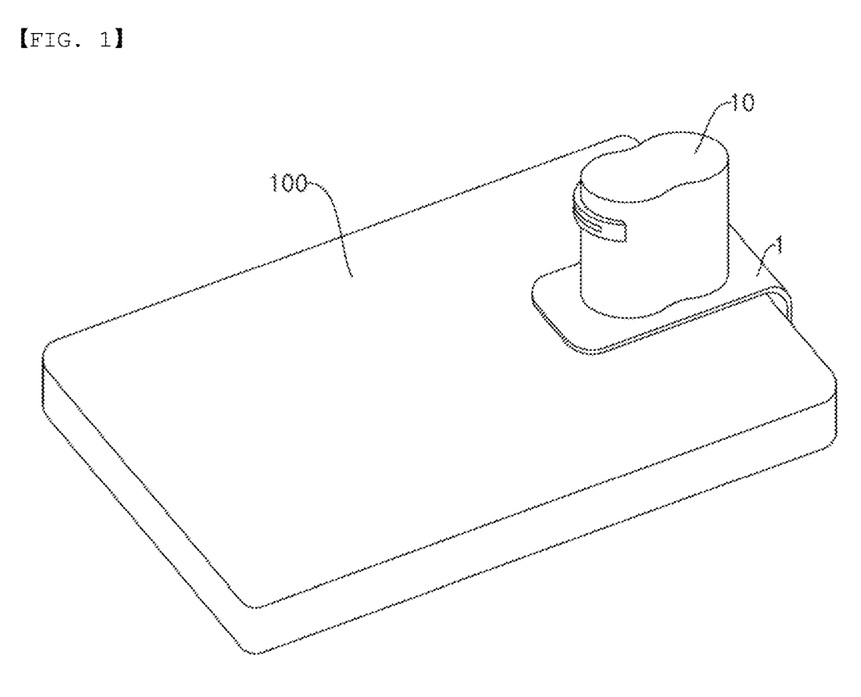
FIG. 1 is a view showing an example of use of a testing device.
Figure 2:
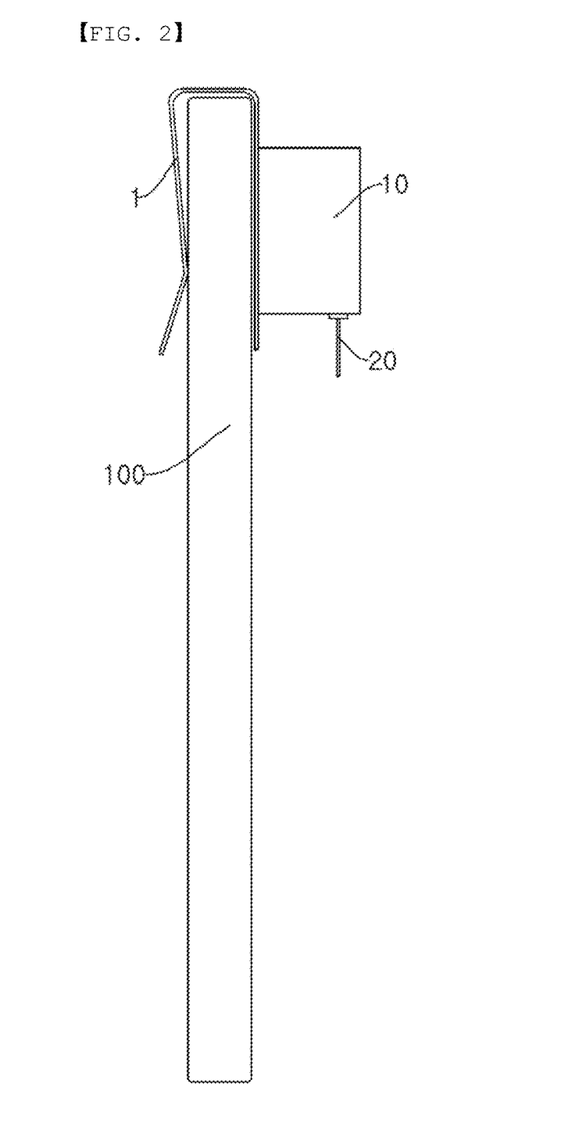
FIG. 2 is a side view showing an example of use of the testing device.

FIG. 1 is a view showing an example of use of a testing device, and FIG. 2 is a side view showing an example of use of the testing device.

With reference to FIGS. 1 to 2, a body fluid testing device having an improved illumination according to the present invention includes a test unit 10, and a user terminal 100 for coupling the test unit to a coupling means.

The test unit 10 of the testing device is attached to the user terminal 100, and provides a magnified image of body fluid so that the user terminal 100 can take an image of the body fluid and analyze the same using the body fluid as a sample. To be more specific, the test unit includes a sample part 20, wherein the sample part 20 is applied with the body fluid of a user and is coupled to the test unit 10. The test unit 10 is operated according to the coupling of the sample part 20 to provide light to the sample part 20 by an illumination, and the user terminal 100 takes an image of the sample part with the light provided thereto by using a camera to obtain an image of the sample. To achieve this, the test unit 10 includes: an illumination and a lens group provided in a casing 11; a coupling means 1 for coupling the detachable sample part 20 to the user terminal 100. The detailed configuration of the test unit and the testing method using the test unit 10 will be described in detail below with reference to other drawings.

In FIGS. 1 and 2, a clip is provided as the coupling means 1, but the present invention is not limited thereto. However, for the sake of convenience of explanation in the first half of the description, the description will be made using the coupling means 1 configured as a clip shape.

The user terminal 100 is coupled with the test unit 10 to take an image of a sample identified through the test unit 10, and performs a predetermined process to determine the user's physical condition. The user terminal 100 is coupled with the test unit 10 by the coupling means 1, and particularly, the camera provided in the user terminal 100 is coupled with the lens group of the test unit 10 to be aligned with each other to obtain an image. As the user terminal 100, any device capable of taking an image by a camera and running an analysis program provided in the form of an application program may be used as well as a mobile terminal such as a user's notebook, a smart phone, or a smart pad.

Figure 3:
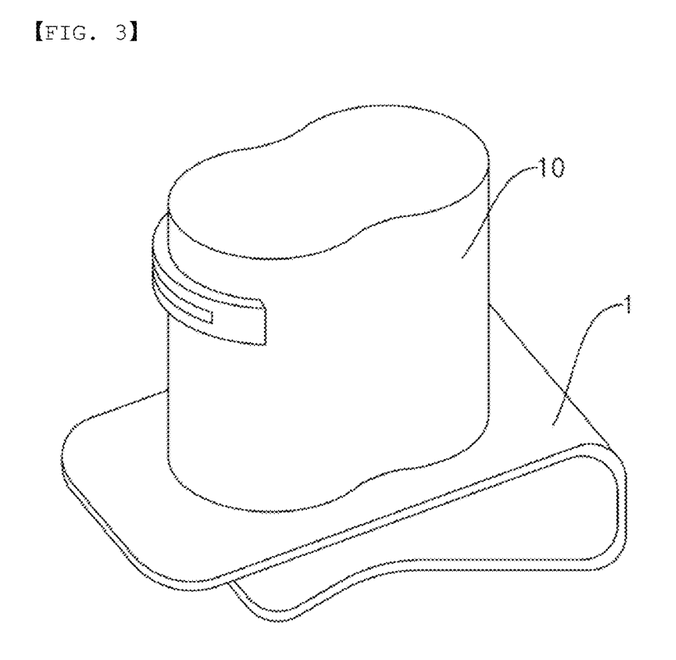
FIG. 3 is a perspective view showing the testing device according to the present invention.
Figure 4:
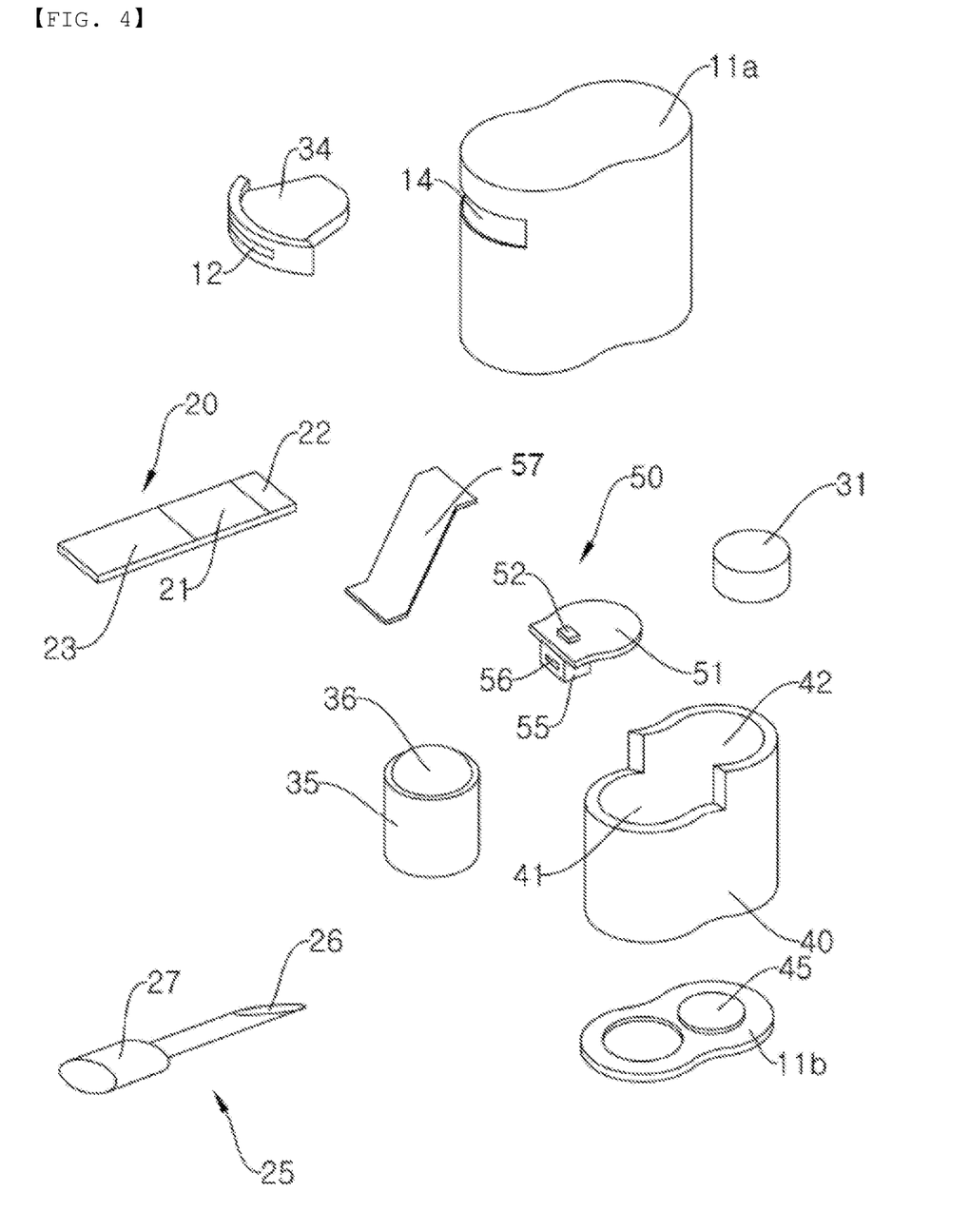
FIG. 4 is an exploded perspective view showing a testing unit.
Figure 5:
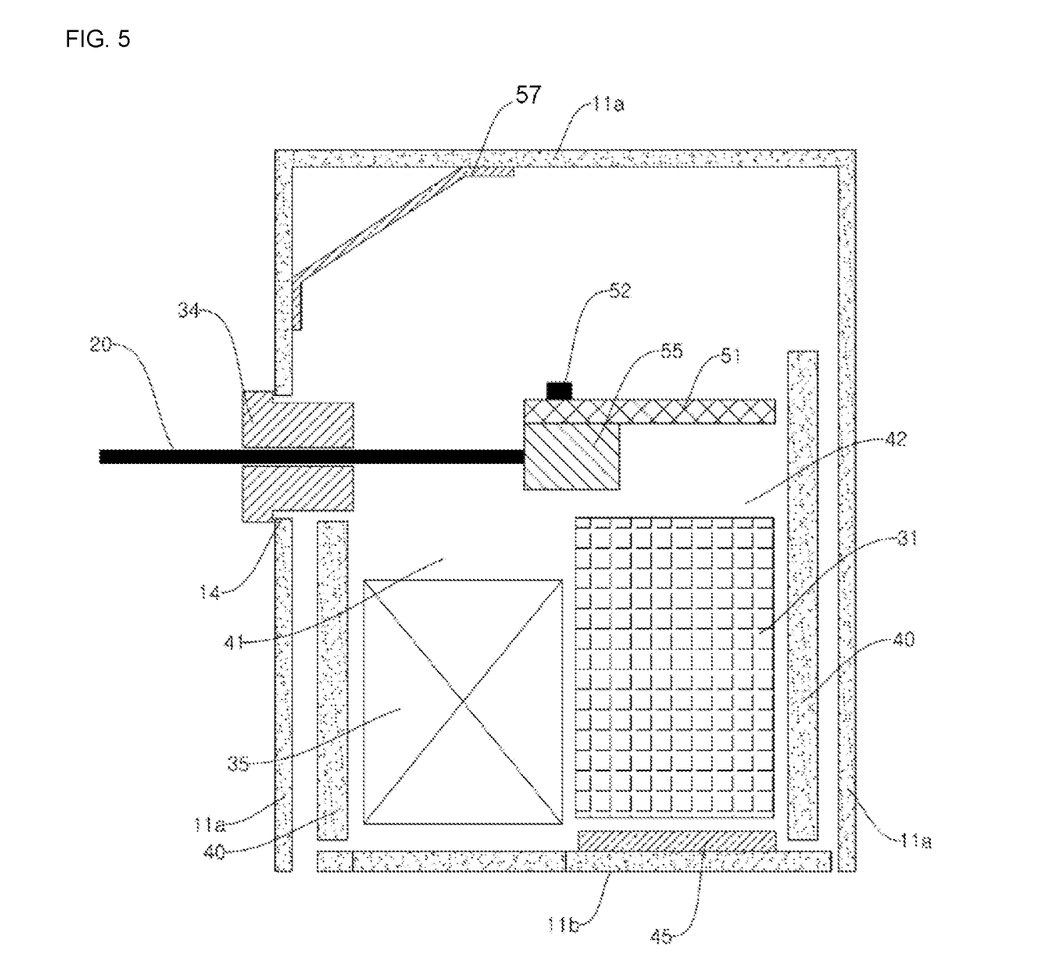
FIG. 5 is an exemplary view schematically showing a cross-section of the test unit.
Figure 6:
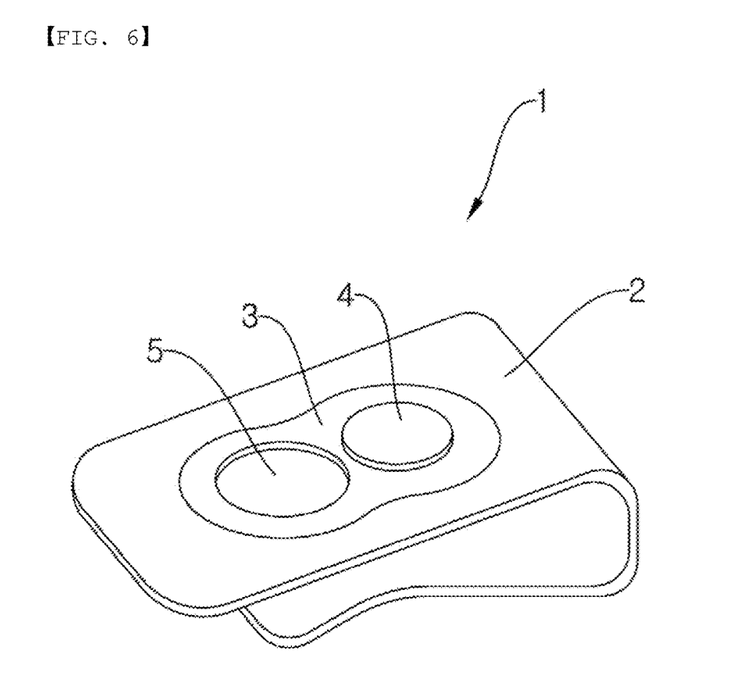
FIG. 6 is an exemplary view showing coupling and decoupling between the test unit and a coupling means.

FIG. 3 is a perspective view showing the testing device according to the present invention, FIG. 4 is an exploded perspective view showing a testing unit, FIG. 5 is an exemplary view schematically showing a cross-section of the test unit, and FIG. 6 is an exemplary view showing coupling and decoupling between the test unit and the coupling means.

With reference to FIGS. 3 to 6, the testing device according to the present invention includes the test unit 10, and the coupling means 1.

The test unit 10 serves as an objective for allowing the user's body fluid used as a sample to be analyzed by the user terminal 100. To be more specific, the test unit 10 is coupled to the user terminal 100 by the coupling means 1, with the body fluid used as a sample applied onto the sample part 20. Here, the test unit 10 is coupled to the user terminal 100 with the camera of the user terminal 100, and the lens and the sample part 20 of the test unit 10 aligned with each other, such that that user terminal 100 takes an image of the body fluid magnified by the lens. Then, the user terminal 100 analyzes the image of the body fluid through analyzes the image of the body fluid through a process of a predetermined program and determines the user's physical condition.

The test unit 10 is detachably coupled to the user terminal 100 by the coupling means 1, as shown in FIG. 6. To be specific, the coupling means 1 is formed in a clip shape, wherein the coupling means 1 may be configured to be coupled to the test unit 10 so as not to be separated, but may be configured to be easily detachable from the test unit as shown in FIG. 6. To be specific, the test unit 10 and the coupling means 1 may be detachable to each other by using a means as a magnet capable of repetitive attachment and detachment such. In FIG. 6, a case is shown in which an iron piece 4 to be coupled with the magnet is provided in a clip main body 2 of the coupling means 1. The iron piece 4 is coupled to or separated from the magnet 45 provided in a lower casing 11b of the test unit 10 by a magnetic force so that the test unit 10 is detached from and attached to the coupling means 1. Herein, the coupling means 1 may also be provided with a magnet, which means that the magnet is provided in the coupling means 1, and the iron piece is provided in the test unit 10 instead of the magnet 45, but the present invention is not limited to the above configuration.

The coupling means 1 couples the test unit 10 with the user terminal 100, and allows a contact portion 37 of the test unit 10 to be aligned with the camera of the user terminal 100. To achieve this, the coupling means 1 includes: the clip main body 2 having elasticity; and the iron piece 4 coupled to the clip main body 2 to hold the test unit 10. The clip main body 2 is configured such that a plurality of portions thereof is curved (or bent), and is formed of a material having an elastic restoring force such as synthetic resin or metal. The clip main body 2 is provided with a mounting portion 3 to be coupled with the test unit 10, and the mounting portion 3 is provided with a means such as the iron piece 4 for coupling the coupling means 1 and the test unit 10 together or separating the same from each other. Further, the mounting portion 3 is provided with a clip hole 5 formed through the mounting portion 3. The lens group 35 of the test unit 10 and the camera of the user terminal 100 face each other through the clip hole 5.

The test unit 10 is coupled to the user terminal 100 by the coupling means 1 and provides an illumination and a magnifying means for the body fluid applied onto the sample part 20. The user terminal 100 allows an image of the body fluid to be obtained by the magnifying means and the illumination. As described above, the test unit 10 is operated to provide light to the sample part when the sample part 20, with the body fluid applied thereonto, is inserted, so that a clear image of the body fluid can be taken by the camera of the user terminal 100. To achieve this, the test unit 10, to which the sample part 20 is coupled, includes: a lens group 35 for magnifying the body fluid applied onto the sample part 20; a light source 52 for allowing the clear image of the body fluid to be obtained; a circuit board 51 for sensing the operation of the light source 52 and insertion of the sample part 20; and a battery 31 for supplying power. In particular, the test unit 10 is provided with a light scattering means such as a light guide means or a reflector 57 so that uniform light can be transmitted to the sample part 20, and is further provided with a sample collection means for easily applying the body fluid onto the sample part 20.

To be specific, the test unit 10 includes: an upper casing 11a; a lower casing 11b; the sample part 20; the lens group 35; the battery 31; an inner frame 40; and an illumination part 50.

The upper casing 11a receives the sample part 20, the lens group 35, the battery 31, the inner frame 40, and the illumination part 50 therein, and protects against external impact or pollution. The upper casing 11a is coupled with a sheet mounting portion 34 for insertion and supporting of the sample part 20, and is formed with a casing hole 14 for coupling the sheet mounting portion 34. Although not shown in the drawing, a display window may be formed to emit the light of the light source 52 to the outside in order to display the operation state to the outside, but this does not limit the present invention. The upper casing 11a may be formed of a material that is mechanically rigid, such as metal or synthetic resin, and may be coupled with the lower casing 11b to accommodate components therein. Inside the upper casing 11a, that is, between the inner frame 40 and the upper casing 11a, the reflector 57 or the light guide means may be provided.

The sample part 20 is inserted through an insertion hole 12 formed in the sheet mounting portion 34 and is inserted into an insertion port 56 of the illumination part 50. The sample part 20 is constituted by a sheet portion 21, an electrode portion 22, and a body portion 23, wherein the body fluid of a user is applied onto the sheet portion 21. When the sample part 21 with the body fluid of the user applied onto the sheet portion 21 is inserted into the insertion port 56, an electrode of an insertion module 55 is connected by the electrode portion 22, whereby the test unit 10 is operated. To achieve this, the electrode portion 22 may be electrically connected to the electrode formed inside the insertion module 55, and may be formed with a pattern for forming a circuit by connecting a plurality of electrodes in a predetermined shape. The electrode portion 22 may be formed by forming a metal thin film on the body portion 23, or may be formed using a conductive material such as carbon.

The sheet portion 21 is provided at a portion of the body portion 23, and the body fluid of the user is applied onto the sheet portion. The position of the sheet portion 21 is determined to be positioned at the focal length of the lens group 35. The user applies the body fluid thinly and uniformly on the sheet portion 21 using the sample collection means. The sheet portion 21 may be integrally formed with the body portion 23 and is formed to be transparent so that the body fluid can be imaged and identified. However, a predetermined monochromatic color, such as green and yellow, may be applied to obtain a clear image when taking an image of the body fluid, but this does not limit the present invention.

The body portion 23 allows the user to grip the sample part 20. The body portion 23 is integrally formed with the sheet portion 21 and the electrode portion 22, and may be provided with a film or an anti-slip coating layer to facilitate the user to distinguish the sheet portion 21 and to prevent slip when gripping. The body portion 23 may be formed of a transparent synthetic resin such as polyethylene or acrylic, or formed of glass, and when coloring is applied to the sheet portion 22, the same coloring may be applied to the body portion 23, but the present invention is not limited thereto.

The sheet mounting portion 34 serves to guide the electrode portion 22 of the sample part 20 toward the insertion port 56 of the insertion module 55 provided in the illumination part 50 when the sample part 20 is inserted, and is configured to support the inserted sample part 20. The sheet mounting portion 34 may be formed of synthetic resin, and is coupled to the casing hole 14. In particular, the sheet mounting portion 34 may be formed of transparent or translucent synthetic resin so that when the light source of the illumination part 50 is turned on, the light of the light source can be emitted to the outside to allow the user to recognize whether it is performed, and to improve the aesthetics, but the present invention is not limited thereto. The sheet mounting portion 34 is formed with the insertion hole 12 for allowing the sample part 20 to be inserted therethrough.

The lens group 35 is provided as a means for magnifying the body fluid applied onto the sheet portion 21 of the sample part 20. The lens group 35 is composed of a combination of a plurality of lenses 36, and is coupled to a lens housing portion 41 of the inner frame 40 and housed inside the casing 11: 11a and 11b. The lens group 35 is disposed such that the sheet portion 21 of the sample part 20 is located at one side focal length of the lens group 35 and the other side is directed toward the contact portion 37. The lens group 35 faces the contact portion 37 of the user terminal 100 to allow the camera to take an image of the magnified body fluid.

The inner frame 40 fixes the lens group 35, the illumination part 50, the battery 31, etc., and is accommodated inside the upper casing 11a. For fixing the position of each configuration and for convenience of production, in the present invention, the inner frame 40 is configured to be separable from the upper casing 11a. However, the inner frame 40 may be integrally formed with the upper casing 11a or the lower casing 11b. This configuration is provided for convenience of explanation and the present invention is not limited thereto. The inner frame 40 includes the lens housing portion 41, and a power receiving portion 42, wherein the lens housing portion 41 and the power receiving portion 42 may be provided side by side by a wall formed therebetween.

The lens group 35 is disposed by being inserted in the lens housing portion 41 of the inner frame 40, and the battery 31 is accommodated in the power receiving portion 42. The lens housing portion 41 of the inner frame and the power receiving portion 42 may have different heights as shown in FIG. 4, and for example, the height of the lens housing portion 41 may be shorter than that of the power receiving portion 42. Thereby, the illumination part 50 may be coupled to the upper portion of the power receiving portion 42 formed to be higher than the lens housing portion 41. Thus, the insertion module 55, into which the sample part 20 is inserted, is positioned at a position above the lens group 35 so that the sheet portion 21 of the sample part 20 to be inserted into the insertion module 55 is naturally positioned in the focus direction of the lens group 35.

The battery 31 supplies power to the illumination part 50 that is accommodated in the power receiving portion 42 and is disposed thereabove.

The illumination part 50 provides light to the sample part 20 so that the camera of the user terminal 100 can obtain the clear image of the body fluid applied onto the sample part 20. Although the illumination part 50 may be driven using a separate switch, it may be advantageous in terms of ease of use that the illumination part is driven by detecting insertion of the sample part 20. As described above, the illumination part 50 may be coupled to the inner frame 40 to be disposed above the battery 31 of the power receiving portion 42 provided in the inner frame 40. Further, the illumination part 50 is electrically connected to the battery 31 accommodated in the power receiving portion 42 to receive power. The illumination part 50 may be provided with a separate switch as described above, but may be configured to be driven such that the light source 52 emits light when the sample part 20 is inserted in the insertion module 55. To achieve this, the illumination part 50 includes the circuit board 51, the light source 52, and the insertion module 55.

The circuit board 51 serves as a structure for fixing the illumination part 50 to the inner frame 40 and for installing the light source 52 and the insertion module 55. The circuit board 51 is formed in a shape corresponding to the shape of the power receiving portion 42, and may be coupled to the inner frame 40 by being inserted therein. The circuit board 51 may be configured such that one surface thereof is provided with the light source 52 and the other surface thereof is provided with the insertion module 55, but the present invention is not limited thereto. Although not shown, the circuit board 51 may be provided with an electrode for electrical connection with the battery 31. The circuit board 51 includes a circuit for electrically connecting the insertion module 55, the battery 31, and the light source 52 together. This circuit may be configured such that a partial short circuit is formed by an insertion module 55. Thus, the circuit board 51 allows the light source 52 to be supplied with power when a short circuit forms a closed circuit by the electrode portion 22 of the sample part 20 so that the light source emits light.

The light source 52 emits light by being supplied with power from the battery 31 by the circuit board 51. The light source 52 is composed of a light emitting element such as a light emitting diode and emits monochromatic light or white light.

The insertion module 55 is provided with an insertion port 56 into which the electrode portion 22 of the sample part 20 is inserted, and the insertion port 56 is provided with a plurality of electrical terminals in electrical contact with the electrode portion 22. The electrical terminals (not shown) of the insertion module 55 are mounted in the circuit board 51 to be electrically connected to the circuit provided on the circuit board 51. When the sample part 20 is not inserted, the electrical terminals form a short circuit to maintain the open circuit state, and when the sample part 20 is inserted, the electrical terminals form a closed circuit by the electrode portion 22 and serve to conduct electricity. In other words, when the sample part 20 is inserted into the insertion module 55, a closed circuit is formed to complete the circuit that supplies power to the light source 52, and thus, the light source 52 is automatically caused to emit light. In particular, the arrangement of the electrical terminals and the shape of the conductive pattern formed in the electrode portion 22 can be used as a means for authenticating the sample part 20. In other words, when the sample part 20 having the electrode portion 22 that does not match the electrical terminals formed on the insertion module 55 is used, the operation is not performed, so activation of the sample part 20 is possible without having a separate authentication means.

The lower casing 11b serves to receive and fix the inner frame 40 by being coupled to an opened portion of the upper casing 11a, and allows the test unit 10 to be detachable from the coupling means 1. To achieve this, the lower casing 11b may be coupled with the magnet 45, which provides a magnetic force to the iron piece 4 provided in the coupling means 1, or the lower casing 11b may be provided with the iron piece 4 and the coupling means 1 may be provided with the magnet 45.

The reflector 57 is coupled to an inner side of the upper casing 11a or an end of the inner frame 40, and serves to reflect the light emitted from the light source 52 to the sample part 20. Thus, the reflector 57 allows the light emitted from the light source 52 to be sufficiently scattered within the casing 11 to illuminate the sample part 20 such that uniform light is provided to the sample part 20, and thus the camera of the user terminal 100 obtains a clear image of the body fluid. The reflector 57 may be configured such that one or more portions are bent according to the positional relationship between the mounting position thereof and the light source 52, and may be formed of metal or glass, but the present invention is not limited thereto. In addition, the surface of the reflector 57 may be processed to form the uneven surface for scattering of light.

Further, the test unit 10 according to the present invention may include a sample collection means. The sample collection means 25 is constituted by a handle 27 and a spatula 26, so that the user can scratch the body fluid on the body using the spatula or collect the discharged body fluid and apply the body fluid to the sheet portion 22. Here, the sample is obtained by the spatula 26 and is applied onto the sheet portion 22. To achieve this, the longitudinal end of the spatula 26 may be formed to be inclined, and the inclined surface may be formed to be flat.

Figure 7:
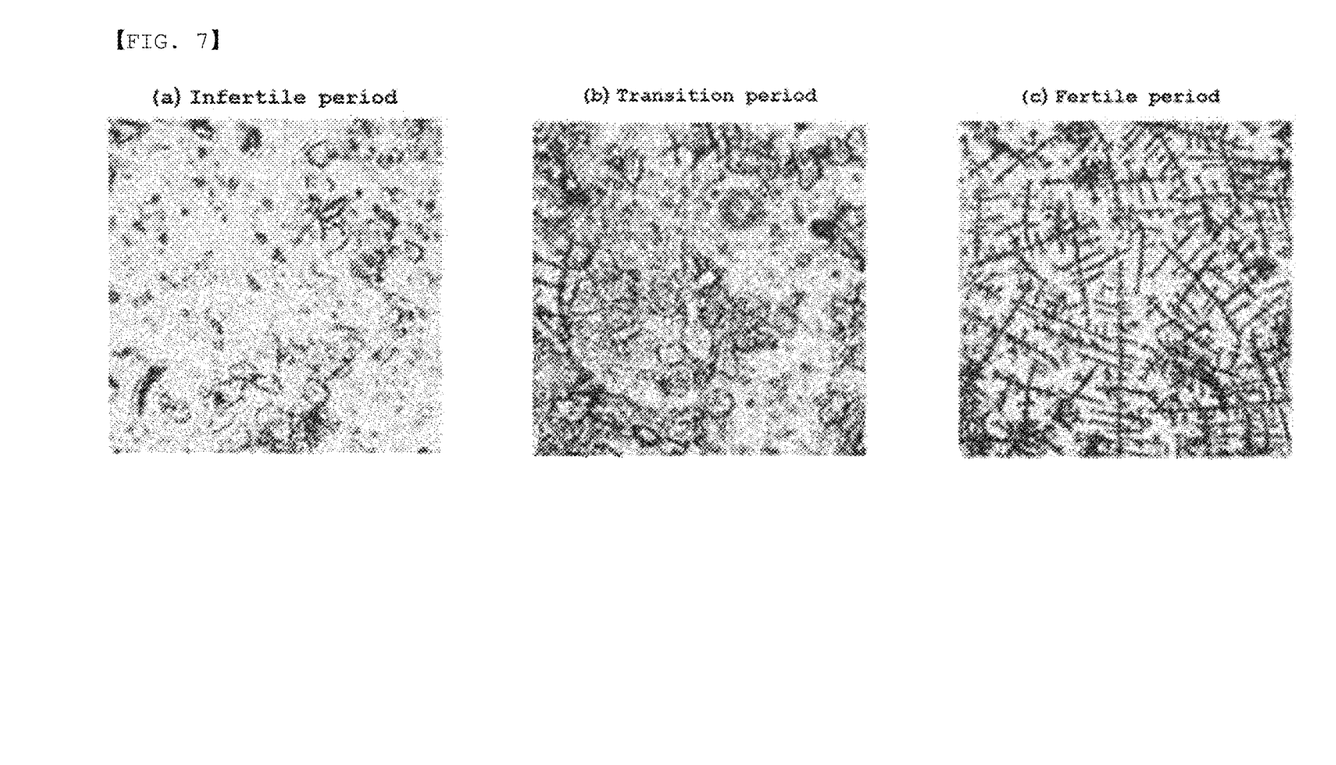
FIG. 7 illustrates exemplary views showing change in body fluid for pattern analysis.
Figure 8:
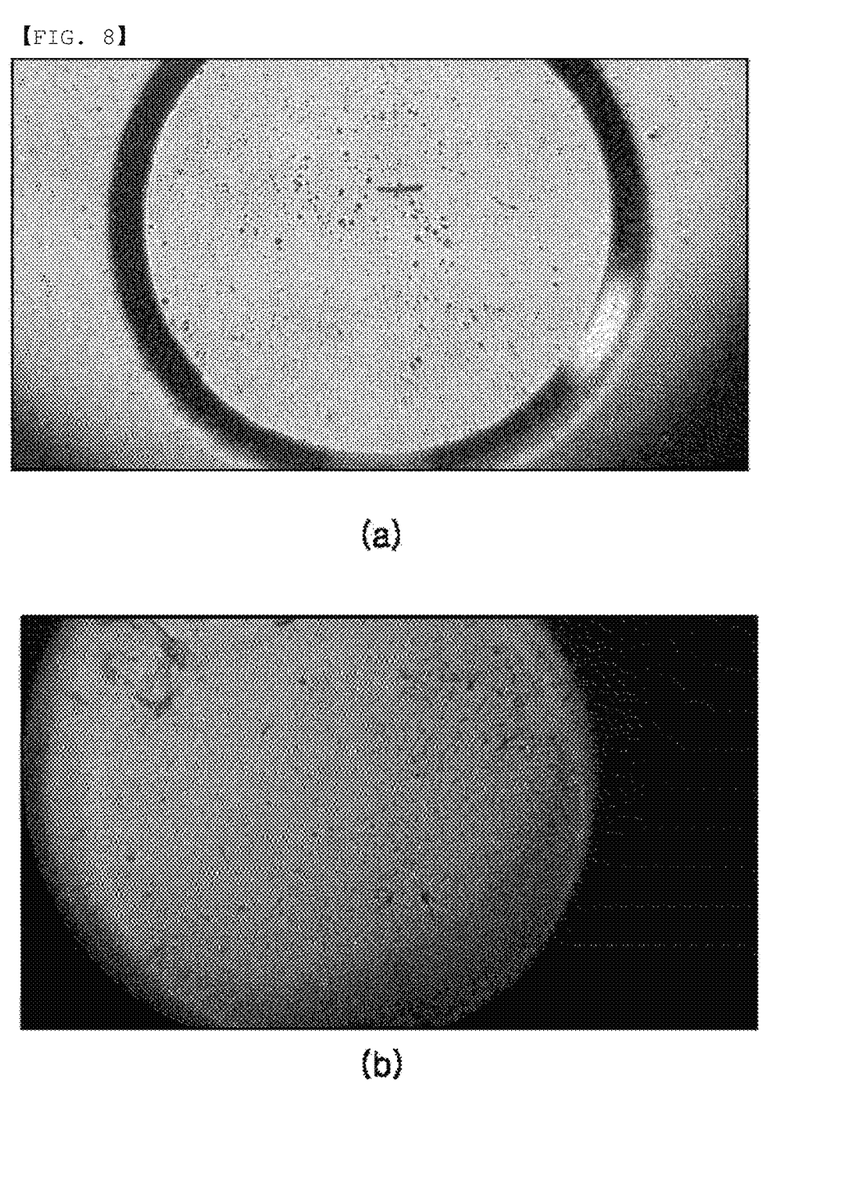
FIG. 8 illustrates exemplary views showing test images in which actual body fluid is used.
Figure 9:
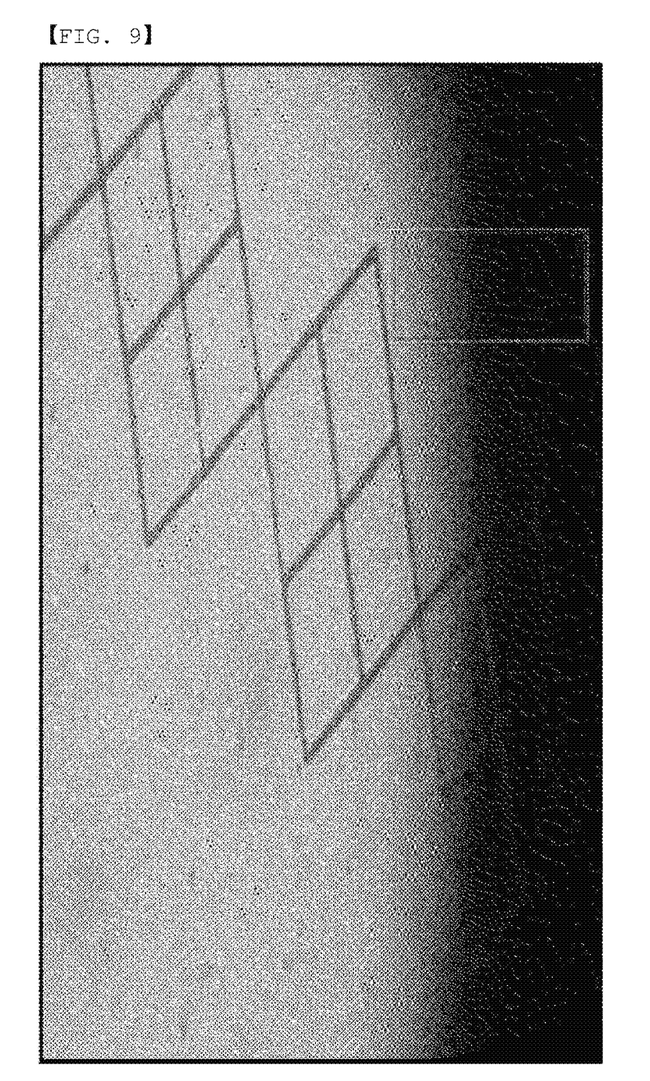
FIG. 9 is a view showing an example of a subdivision pattern for analysis of the test image.

FIGS. 7 to 9 are exemplary views illustrating a pattern analysis method according to the present invention. FIG. 7 illustrates exemplary views showing change in body fluid for pattern analysis, and FIG. 8 illustrates exemplary views showing test images in which actual body fluid is used. Also, FIG. 9 is a view showing an example of a subdivision pattern for analysis of the test image.

With reference to FIGS. 7 to 9, the body fluid, particularly, the saliva may be used as an indicator of various conditions. Herein, in the present invention, the body fluid refers to various liquids that are secreted from a human body and substances contained therein such as epithelial cells, urine proteins, hormones, and salts. To be more specific, the body fluid may be liquids such as saliva, vaginal discharge, semen, urine, and sweat, or substances contained therein. The saliva of a woman in the fertile period shows a special sign distinctly. Specifically, due to the influence of estrogen which is a female hormone contained in the saliva of a woman, ovulation may be accurately predicted, and thus married couples suffering from infertility may increase pregnancy probability.

To be specific, when a woman is in the fertile period, as the ovulation date gets closer, the secretion rate of the estrogen increases, and also, the salt concentration of the saliva increases. Accordingly, when the saliva is dried for a particular time, different crystal structures of the dried saliva are shown depending on the infertile period, the transition period, and the fertile period.

For example, when drying and photographing the saliva of the woman in the infertile period during which ovulation does not occur, an image in which no distinct crystal structure is found is obtained as shown in FIG. 7(*a*).

FIG. 8(*a*) shows the actually obtained image. As shown in FIGS. 7(*a*) and 8(*a*), in the infertile period, no specific crystal structure is found, and only some salivary cells are identified.

In the transition period during which the infertile period transitions to the fertile period in which ovulation occurs, the saliva of the woman is slightly crystallized in the form as shown in FIG. 7(*b*). At this time, the form of the crystals is the form of salivary cells in circular and oblong shapes formed by electrolyte, mucus, enzyme, etc.

Last, in the fertile period during which ovulation occurs, the form in which the crystal extends in one direction, namely, a fern pattern clearly visible as shown in FIG. 7(*c*). FIG. 8(*b*) shows an image of actual saliva of the woman in the fertile period. As seen from this, the pattern distinctly distinguished from FIG. 8(*a*) is identified.

In the body fluid testing device of the present invention, the state of the saliva is analyzed to identify whether the user is in the fertile period, and the identified information is provided to the user as the analysis information.

In other words, the user terminal 100 performs image processing on the obtained test image to clarify the crystal line, and determines whether the crystal line is in the form of a closed curve line or in the form of the straight lines in the fern pattern as shown in FIG. 7(*c*). Particularly, the length and density of the linear pattern is identified. Consequently, the infertile period, the transition period, and the fertile period are determined and the result is provided to the user as the analysis information. Here, the image processing and the determining of the infertile period, the transition period, and the fertile period are possibly adjusted depending on the density and form of the pattern, and thus the detailed description thereof will be omitted.

Further, in image processing, the image is reprocessed in black and white, and the contrast of black and white is distinguished to determine the form of the line, whereby the length and the density is determined. Since various methods may be used, the detailed description thereof will be omitted.

In the meantime, in order to enhance accuracy of image processing and the determination, a subdivision pattern may be used as shown in FIG. 9. That is, how many straight lines or oval lines are present in the region (the region inside the closed line) defined by the pattern is identified, and the analysis information is generated.

In particular, the subdivision pattern may be provided in a printed form on the lens group 35 of the user terminal 100 or on the sample part 20, or a part of the analysis image may be partitioned in the subdivision pattern by the user terminal 100 for image processing, but the present invention is not limited thereto.

Figure 10:
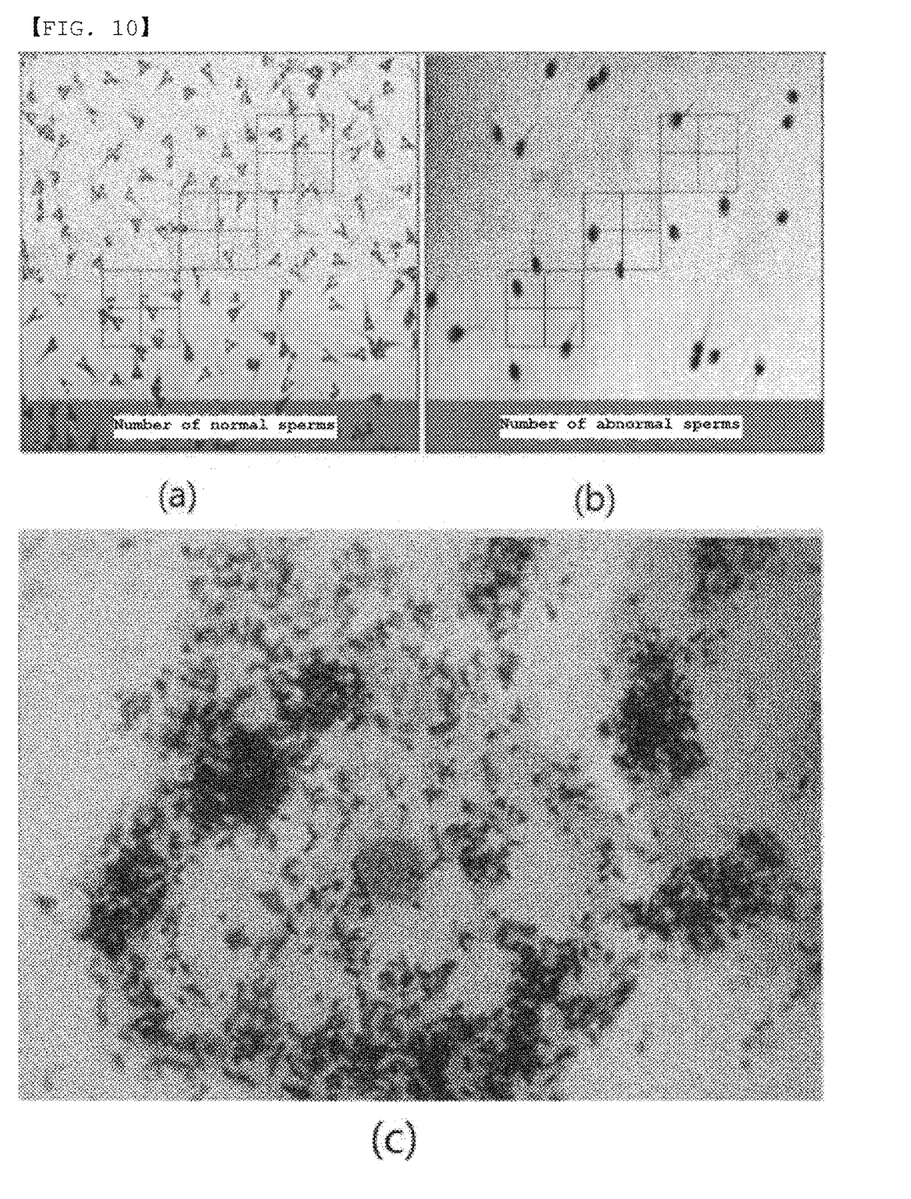
FIG. 10 illustrates views showing an example of a case where the body fluid is semen or vaginal discharge.

Meanwhile, FIG. 10 illustrates views showing an example of a case where the body fluid is semen or vaginal discharge.

The analysis information may be generated with respect to semen of a man. When using the body fluid testing device of the present invention with respect to semen of a man, matters that the number of sperms, sperm activity, and whether sperms have deformity may be identified. Particularly, after improving the state of sperms, it is possible to try to get pregnant.

In analyzing semen, the subdivision pattern may be used as shown in FIGS. 10(*a*) and (*b*). By determining the number, activity, and the form of sperms positioned within the grid pattern formed in the middle of FIGS. (a) and (b), the sperm characteristic is easily analyzed. To be more specific, all sperms distributed throughout the obtained image are not analyzed by the user terminal 100 or a medical institution system (not shown), sampling analysis may be performed on targets that are sperms in the region delimited by the subdivision pattern. According to the present invention, quick analysis is possible, and pattern processing load of the user terminal 100 may be reduced with more detailed analysis.

As an example of the subdivision pattern, although the grid form is shown in FIGS. 9 and 10, the pattern may be formed in various shapes, such as an oval, a circle, etc., and an arbitrary position may be specified as well as the center of the screen. Also, the image is checked, and the subdivision pattern is applied to the position with high density, whereby the analysis is conducted. The present invention is not limited thereto.

In order to analyze the sperm characteristic in the user terminal 100 of the present invention, a similar method to the above-described saliva analysis is performed. First, the user terminal 100 photographs the semen deposited on the sample part 20 to obtain the test image. The user terminal 100 computes the number of sperms, travel distances of particular sperms, the average of the travel distances, whether to rotate, the rotation speed, and the rotation radius identified within a particular region in the test image. Here, the user terminal 100 may obtain several test images for use, or may obtain the test image in the form of a video. Here, particular sperms in the image are randomly selected and the sperm characteristic of the randomly selected sperms is determined, whereby the state of sperm is identified. Also, the selection of multiple sperms for sampling may enhance accuracy of the analysis of the sperm characteristic.

Further, the user terminal 100 selects some sperms in the test image, the image of the selected sperms is processed in a clear pattern or in a black-and-white image, and then the result is compared with a pre-stored image or with a pre-determined condition whether to have a shape corresponding thereto, whereby whether sperm is malformed is determined. For example, whether sperms in the test image have a normal form may be identified by determining the number of end portions (tail shape) per head (round part), whether the end portion is bent, and malformation of the head.

In particular, in this process, in order to facilitate selection and sampling of sperms, the subdivision pattern is applied as shown in FIG. 10, and the sperm characteristic may be analyzed by targeting the sperms positioned in the region defined by the subdivision pattern among sperms in the test image. Thus, selection of sperms for sampling may be easy, consistency of the analysis information may be maintained, and the load of the user terminal 100 due to the analysis may be reduced, whereby quick analysis is possible.

Also, as shown in FIG. 10(c), the vaginal discharge is observed to determine the presence of disease symptoms, such as bacterial vaginosis, vaginitis, and whether to perform diagnosis. Specifically, when the vaginal discharge is observed by using an examination device, only vaginal mucosa cells are observed for a normal case. However, as shown in FIG. 10(c), when a disease caused by bacterial infection occurs, substances such as those shown as black spots in FIG. 10(c) are identified. FIG. 10(c) shows the case in which secretion of anti-bacterial substances inside the vagina decreased resulting in an increase of vaginal acidity and overgrowth of anaerobic bacteria. The overgrown anaerobic bacteria is adsorbed on the surface of the vaginal mucosa cell and the vaginal mucosa cells are covered with black spots, and the symptom is identified by the examination device. As a result, according to the present invention, body secretion such as the saliva, the vaginal discharge, and the semen of man is photographed in a magnified manner, and an image analysis and a visual analysis are conducted such that various states, such as the presence of the disease, the name of the disease, the ovulation period, are possibly determined.

While the exemplary embodiments of the invention have been described above, the embodiments are only examples of the invention, and it will be understood by those skilled in the art that the invention can be modified in various forms without departing from the technical spirit of the invention. Therefore, modifications of the present invention are appreciated as included in the scope and spirit of the invention, and the protection scope of the present invention will be defined by the accompanying claims.

The invention claimed is:

1. A body fluid testing device having illumination, the testing device comprising:
   a test unit including:
      a sample part having a sheet portion, with body fluid of a user configured to be applied onto a first surface thereof;
      a casing hole;
      a sheet mounting portion coupled to the casing hole and formed with an insertion hole for allowing the sample part to be inserted therethrough;
      an illumination part having an insertion module formed with an insertion port to receive the sample part and a light source for providing light to the sample part, wherein the sample part comprises an electrode portion provided with a conductive pattern;
      a battery for supplying power to the illumination part;
      a casing receiving a lens group for magnifying the body fluid applied onto the sheet portion; and
      a reflector provided in an inner side of an upper casing to reflect the light emitted from the light source to the sheet portion; and
   a user terminal comprising a camera to take an image of the sample part magnified by the lens group, prior to analyzing the image by the user terminal,
   wherein the conductive pattern of the electrode portion is configured to form a closed circuit when the sample part is inserted into the test unit, wherein the closed circuit supplies power of the battery to the light source to cause the light source to automatically emit the light to the sheet portion when the sample part is inserted into the test unit.

2. The testing device of claim 1, further comprising:
   a coupling means detachably coupled to the test unit,
   wherein the test unit is detachably coupled to the user terminal by the coupling means, and
   the coupling means has a mounting portion which the test unit is configured to be mounted to and is provided with a clip hole at a position between the lens group of the test unit and the camera, the coupling means being formed in a shape of a clip.

3. The testing device of claim 2, wherein one of the test unit and the coupling means is provided with a magnet at a mutual contact portion, and a remaining one of the test unit and the coupling means is provided with a magnet or an iron piece.

4. The testing device of claim 1, wherein the sample part is configured such that a longitudinal end thereof to be inserted into the insertion module is provided with the conductive pattern for completing the circuit for connection of the light source and the battery by being electrically connected to an electrical terminal provided on the insertion module.

5. The testing device of claim 1, further comprising:
   a sample collection means for collecting the body fluid and applying the body fluid onto the sheet portion.

* * * * *